(12) United States Patent
Brown et al.

(10) Patent No.: US 7,257,196 B2
(45) Date of Patent: Aug. 14, 2007

(54) RADIOTHERAPEUTIC APPARATUS

(76) Inventors: Kevin John Brown, 200 New Street, Horsham, West Sussex (GB) RH13 5EJ; David Anthony Jaffray, 2476 Lincoln Road, Windsor, Ontario (CA) N8W 2R7

( * ) Notice: Subject to any disclaimer, the term of this patent is extended or adjusted under 35 U.S.C. 154(b) by 0 days.

(21) Appl. No.: 10/469,481

(22) PCT Filed: Feb. 27, 2003

(86) PCT No.: PCT/GB02/00789

§ 371 (c)(1), (2), (4) Date: Aug. 27, 2003

(87) PCT Pub. No.: WO02/069349

PCT Pub. Date: Sep. 6, 2002

(65) Prior Publication Data

US 2004/0096038 A1    May 20, 2004

(30) Foreign Application Priority Data

Feb. 27, 2001 (GB) .................................. 0104761.2

(51) Int. Cl.
*G21K 1/02*  (2006.01)

(52) U.S. Cl. .......................... 378/150; 378/65; 378/152

(58) Field of Classification Search ................ 378/145, 378/147, 150, 151, 152, 65
See application file for complete search history.

(56) References Cited

U.S. PATENT DOCUMENTS

| 3,088,031 | A | 4/1963 | Varga et al. ................ 250/105 |
| 4,490,835 | A * | 12/1984 | Wons .......................... 378/146 |
| 5,596,619 | A | 1/1997 | Carol .......................... 378/65 |
| 6,266,393 | B1 * | 7/2001 | Ein-Gal ..................... 378/152 |

FOREIGN PATENT DOCUMENTS

| JP | 63 225199 | 9/1988 |
| JP | 01 206300 | 8/1989 |
| JP | 06 210012 | 8/1994 |
| JP | 2514025 B2 * | 7/1996 |
| JP | 11216196 A * | 8/1999 |

* cited by examiner

*Primary Examiner*—Edward J. Glick
*Assistant Examiner*—Chih-Cheng Glen Kao
(74) *Attorney, Agent, or Firm*—Bromberg & Sunstein LLP

(57) ABSTRACT

A radiotherapeutic apparatus employs a collimator (52) set below a radiation source (50) and is adapted to move along an arc (54) substantially centered on the radiation source (50). As it sweeps the arc, the collimator (52) is adjusted so as to define the appropriate shape of radiation beam. A continuous sweep over the patient avoids edge artefacts and localized accumulation of leakage.

13 Claims, 1 Drawing Sheet

RADIOTHERAPEUTIC APPARATUS

FIELD OF THE INVENTION

The present invention relates to a radiotherapeutic apparatus.

BACKGROUND ART

A collimator marketed by Nomos Corporation; US., consist of two rows of binary collimators called vanes. Each vane can be in or out and typically covers an area of 1 cm by 1 cm when projected to the patient. These two rows cover an area of 20 cm by 2 cm. Usually the collimator is rotated around the patient and the vanes moved in and out of the radiation field in order to modulate the intensity of the radiation and create the desired dose distribution inside the patient. The system is illustrated in U.S. Pat. No. 5,596,619.

At the completion of the irradiation, one longitudinal slice of the patient has been irradiated and the patient is moved longitudinally (indexed) to the position for the next slice. This motion needs to be very precise as inaccuracies lead to over or under dosages in the tumour and might jeopardise the patient's outcome.

SUMMARY OF THE INVENTION

The present invention provides a radiotherapeutic apparatus comprising a source of radiation, a collimator comprising a plurality of moveable elements arranged to selectively modulate radiation emitted by the source, the collimator being moveable along an arc centred substantially on the radiation source.

Thus, the collimator can sweep an arc whilst modulating the radiation. This would be done while the gantry and patient are stationary. A new beam orientation is then selected by moving the gantry on which the source and collimator are provided, and potentially the couch on which the patient is supported, and then another sweep is performed. This operation would be performed a number of times.

The principal advantage of this technique is there are no junction effects, due to the continuous movement of the collimator. This should prevent any unwanted under or over dosages.

In the Nomos system, the longitudinal resolution of the indexing method is inherently limited by the length of the vanes in that direction (half the index step). With the present invention, the vanes can be opened and shut at any time in the sweep, removing this limitation. Furthermore the positions at which the vanes are opened and shut can be independent for the different beam orientations.

As the indexing has had to be so precise in known arrangements, this has often required that the operators enter the room. This is in principle undesirable for health and safety reasons. According to the present invention, the mechanism will be part of the collimator of the linac such user intervention will not be required.

The known indexing technique forces all incident beam orientations to have the same couch angle—typically zero. This limits the scope for optimisation of beam orientations. It has been shown that allowing other orientations in general improves the optimisation of the dose distribution. The present invention does not have these constraints and all beam orientations normally available for radiotherapy can be used.

The collimator used in the invention can be similar to that of the Nomos system, ie one comprising a plurality of beam segments each associated with a moveable element adapted to selectively block the beam segment. Typically, the beam segments are arranged in an array, such as a linear array or a 2*n array. The moveable elements can take up one of two available positions, one located within the array and thus adapted to block the beam segment, and one located outside the array. In this case, it is preferred that the collimator is adapted to move transverse to both the beam axis and the array length.

The collimator can also be a multi-leaf collimator. These comprise elongate leaves which can be moved into the path of the beam by a desired length. Thus, each leaf modulates the width of the beam at that point. Typically, two arrays of leaves are provided, one on either side of the beam, each having a plurality of leaves disposed in a generally parallel arrangement. In this case, it is preferred that the collimator moves transverse to both the beam axis and the length of the leaves. Thus, a particular non-treated location on the patient will be shielded by a succession of leaves as the collimator moves, each leaf moving as the collimator moves thereby following the outline of the volume to be treated.

MLCs are now extensively used for intensity modulated therapy. In general the trajectory of each leaf is modified to create a dose fluence that creates the desired dose distribution inside the patient. In known systems, there is no possibility of optimising the dose distribution in the direction orthogonal to the leaf travel. This can only be improved by MLCs with thinner leaves and in general more leaves (to cover the same treatment field size). According to aspects of the invention, an MLC is swept in (for example) an arc in a direction orthogonal to the leaf travel. While the MLC is being swept the leaves move in a trajectory which allows the cumulative fluence to the patient to be modulated. With known arrangements, a particular point in the patient is always shielded by a particular leaf pair. According to the invention, this same point would be successively shielded by a number of leaf pairs. The number of leaf pairs will determine the resolution of the modulation and will typically be between 5 and 10. This sweep would then be repeated for a number of beam orientations.

In a system according to the present invention employing a multi-leaf collimator, the dose distribution can be optimised according to methods used in Intensity Modulated Arc Therapy (IMAT) techniques.

This arrangement according to the present invention is advantageous as compared to existing MLC techniques since the resolution in the direction of the sweep is unlimited, as the sweep is continuous. The resolution in the direction of the leaves of an MLC is already unlimited, and thus the present invention can give a free choice of resolution in both axes.

In addition, the field size in the direction of motion is not limited by the number of leaves and their width. This simplifies the construction of the collimator. Further, the efficiency of the device, i.e. the ratio between radiation delivered by the linac and dose absorbed by the patient is much higher than the known Nomos collimator (described above) as a much larger area is being treated at any one time.

Existing multi-leaf collimators exhibit edge effects associated with the junctions between leaves—so called 'tongue and groove'. These can be avoided through the present invention. Multi-leaf collimators also leak slightly between leaves, known as interleaf leakage. According to the present invention, this leakage is spread out so that all areas only receive the average leakage. Thus, no one area receives an exceptional leakage.

BRIEF DESCRIPTION OF THE DRAWINGS

Embodiments of the present invention will now be described, by way of example, with reference to the accompanying figures, in which.

DETAILED DESCRIPTION OF THE EMBODIMENTS

Figure 1:
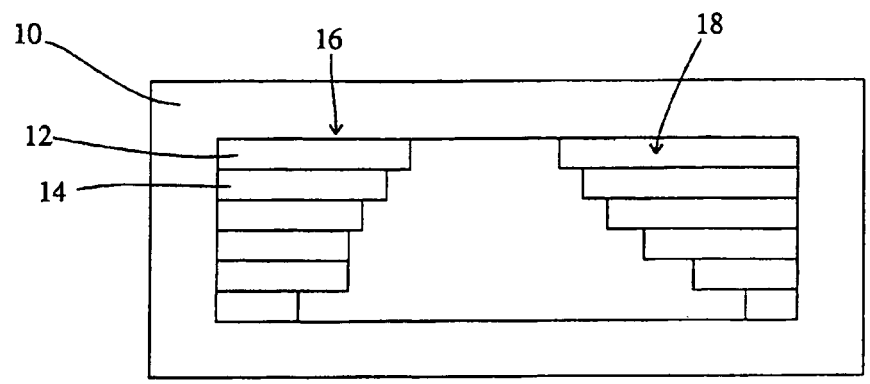
FIG. 1 shows a plan view of a typical multi-leaf collimator.

FIG. 1 shows a typical multi-leaf collimator. A frame 10 carries a number of individual leaves 12, 14 etc. Each of these is supported horizontally within the frame and can move into and out of the field of irradiation which the frame defines. In general, each leaf is driven by a motor and its position is detected for confirmation.

The leaves are arranged in a pair of opposing arrays designated generally as 16 and 18 and thus the two sides of the field can be defined. In known arrangements, the resolution in the direction of the leaves is thus effectively unlimited, whilst the resolution orthogonal to the direction of the leaves is limited by the width of the leaves. This leads to a compromise leaf width, in that a decreased leaf width results in greater resolution, but also to additional engineering difficulties in supporting narrow leaves, and driving each leaf individually to an acceptable accuracy. In general, the use of extremely narrow leaves also tends to result in a physically small collimator which provides only a small aperture.

Figure 2:
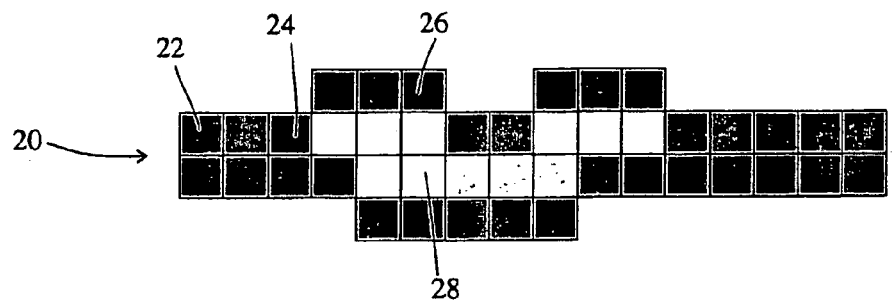
FIG. 2 shows a plan view of a binary collimator.

FIG. 2 shows a binary collimator 20 similar to the Nomos system with a 2×16 array. Other collimators (not shown) limit the field of the radiation to that of the 2×16 array. A plurality of individual pixel elements 22 are moveable into and out of the array, in this example pixel 24 being within the array and pixel 26 being outside. Thus, when the pixel is within the array the radiation is blocked at that point, and when it is outside the array, radiation can pass through that part of the collimator. As shown in FIG. 2, the plurality of individual pixels can be inserted into the array or withdrawn to one side of the array (such as pixel 26) thereby defining a space 28 in which radiation can pass.

Figure 3:
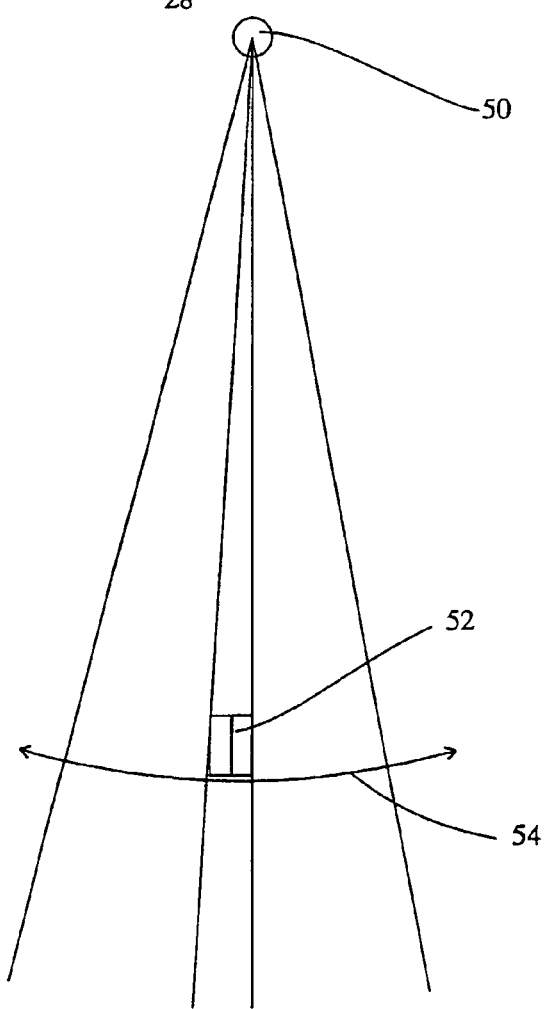
FIG. 3 shows a schematic side view of an arrangement according to the present invention.

FIG. 3 shows schematically the arrangement according to the present invention. A radiation source 50 is provided and would normally be held in a gantry above a patient support table (not shown) below the radiation source. A collimator 52 is also provided beneath the source 50, and can be as per FIG. 1 or FIG. 2, for example. The collimator 52 is supported so that it can swing about an arc 54 which is centred on a radiation source 50. Thus, notwithstanding movement of the collimator along its arc 54, the individual elements of the collimator (pixels or leaves) will remain focussed on the source 50.

As the collimator 52 sweeps along the arc 54, it will selectively irradiate different parts of the patient. During movement, the leaves 12 of the collimator according to FIG. 1 or the pixels 22 of the collimator according to FIG. 2 can be adjusted and operated so as to project the desired radiation beam shape on to the patient. As this is a smooth movement, it avoids edge artifacts and indexing difficulties as set out above.

It will be appreciated that many variations can be made to the above-described embodiments without departing from the present invention.

The invention claimed is:

1. A radiotherapeutic apparatus comprising:
   a source of radiation emitting a beam of therapeutic radiation having a width, and
   a collimator comprising a plurality of moveable elements arranged to limit the beam width by a variable amount, the collimator being moveable along an arc centered substantially on the radiation source and comprising means for moving the beam in a direction transverse to the beam width including means for sweeping the beam to deliver a therapeutic dose of radiation across a two-dimensional area of a patient.

2. A radiotherapeutic apparatus according to claim 1 in which the elements of the collimator are adapted to be adjusted as the collimator is moved.

3. A radiotherapeutic apparatus according to claim 1 in which the collimator comprises an array of moveable elements each adapted to selectively block a beam segment.

4. A radiotherapeutic apparatus according to claim 3 in which the elements are arranged in a linear array.

5. A radiotherapeutic apparatus according to claim 3 in which the elements are arranged in a 2*n array.

6. A radiotherapeutic apparatus according to any one of claims 3 to 5 in which the beam of radiation is emitted along a path passing through part of the array of moveable elements, and the moveable elements can take up one of two available positions, one located within the beam path and thus adapted to block the beam segment, and one located outside the beam path.

7. A radiotherapeutic apparatus according to claim 6 in which the collimator is adapted to move transverse to both a beam axis and an array length.

8. A radiotherapeutic apparatus according to claim 1 or claim 2 in which the collimator is a multi-leaf collimator.

9. A radiotherapeutic apparatus according to claim 8 in which the collimator moves transverse to both a beam axis and a length of leaves of the multi-leaf collimator.

10. A radiotherapeutic apparatus according to claim 1 or claim 2 in which the collimator comprises elongate leaves which can be moved into a path of the beam by a desired length.

11. A radiotherapeutic apparatus according to claim 10 in which two arrays of leaves are provided, one on either side of the beam, each having a plurality of leaves disposed in a generally parallel arrangement.

12. A radiotherapeutic apparatus according to claim 11 in which the collimator moves transverse to both a beam axis and a length of the leaves.

13. A radiotherapeutic apparatus according to claim 10 in which the collimator moves transverse to both a beam axis and a length of the leaves.

* * * * *